United States Patent [19]

Renis et al.

[11] Patent Number: 4,496,587

[45] Date of Patent: Jan. 29, 1985

[54] INHIBITION OF BACTERIAL TOXIN RELEASE BY PROSTAGLANDINS

[75] Inventors: Harold E. Renis, Portage; Mary J. Ruwart, Kalamazoo, both of Mich.

[73] Assignee: The Upjohn Company, Kalamazoo, Mich.

[21] Appl. No.: 488,528

[22] Filed: Apr. 29, 1983

Related U.S. Application Data

[63] Continuation-in-part of Ser. No. 293,899, Aug. 18, 1981, abandoned.

[51] Int. Cl.$^3$ ............................................. A61K 31/19
[52] U.S. Cl. .................................. 514/573; 424/115; 514/530; 514/222; 514/199; 514/198; 514/192; 514/196; 514/207
[58] Field of Search ............... 424/305, 317, 273, 323; 424/115, 271, 246, 228

[56] References Cited

U.S. PATENT DOCUMENTS

| | | |
|---|---|---|
| 4,006,179 | 2/1977 | Bernady et al. ...................... 560/35 |
| 4,081,553 | 3/1978 | Robert . |
| 4,083,998 | 4/1978 | Robert . |
| 4,097,603 | 6/1978 | Robert . |

OTHER PUBLICATIONS

Robert, Gastroenterology 78:1245 (1980).
Derwent Farmdoc Abstract 33613C.
Derwent Farmdoc Abstract 90067C.
Derwent Farmdoc Abstract 87601B.
Derwent Farmdoc Abstract 77055B.
Derwent Farmdoc Abstract 31465B.
Derwent Farmdoc Abstract 19942B.
Derwent Farmdoc Abstract 15606B.
Derwent Farmdoc Abstract 86540Y.
Derwent Farmdoc Abstract 77386Y.
Derwent Farmdoc Abstract 62899Y.
Derwent Farmdoc Abstract 45139Y.
Derwent Farmdoc Abstract 75530X.
Derwent Farmdoc Abstract 73899X.
Derwent Farmdoc Abstract 68620X.
Derwent Farmdoc Abstract 25001X.
Derwent Farmdoc Abstract 42571W.
Derwent Farmdoc Abstract 24030W.
Derwent Farmdoc Abstract 39858V.
Derwent Farmdoc Abstract 03817T.
Flynn–Chem. Abst. vol. 89 (1978) p. 191,560C.
Proctor et al–Chem. Abst. vol. 94 (1981) p. 203,559C.
Schaub et al–Chem. Abst. vol. 80 (1974) p. 59,567V.
Wise et al–Chem. Abst. vol. 94 (1981) p. 154,361W (Article dated 1981).
Reitschel et al–Chem. Abst. vol. 93 (1980) p. 218,942 a.
Proctor et al–Proceed. 4th Int. Cong. Immunol.–Jul. 26, 1980, pp. 273–282.

*Primary Examiner*—Sam Rosen
*Attorney, Agent, or Firm*—Lawrence T. Welch

[57] ABSTRACT

The present invention provides a method for inhibiting the synthesis and release of toxins from bacteria which comprises contacting the bacteria with an antitoxic prostaglandin.

9 Claims, No Drawings

INHIBITION OF BACTERIAL TOXIN RELEASE BY PROSTAGLANDINS

CROSS REFERENCE TO RELATED APPLICATION

This application is a continuation-in-part of Ser. No. 293,899, filed Aug. 18, 1981 now abandoned.

BACKGROUND OF THE INVENTION

The present invention relates to a novel method of treatment of diseases. More particularly, the present invention relates to a novel method of preventing bacterial toxin release and/or synthesis with prostaglandins.

The prostaglandins are derivatives of prostanoic acid. They are useful for a wide variety of pharmacological purposes. See, e.g., Bergstrom, et al., Pharmacol. Rev. 20:1 (1968), and references cited therein. A trivial system of nomenclature has been devised, which classifies the prostaglandins according to the substituents on the cyclopentane ring. See, N. A. Nelson, Journal of Medicinal Chemistry, 17:911 (1974).

Bacterial toxins have been identified as contributing to the pathogenesis of various diseases. Thus, for example, Clostridium difficile (C. difficile) has been associated with the pathogenesis of antibiotic-associated pseudomembranous colitis. Table I lists a number of other diseases for which a bacterial toxin plays a major role.

Previous pharmacological agents have concentrated on protecting the gastrointestinal system from the effects of toxins, through the use of so-called "cytoprotective" agents, or on attacking the bacteria itself. Both approaches have met with limited success.

A third approach to the treatment of bacterial induced diseases is to block the release and/or synthesis of cytotoxin.

PRIOR ART

Numerous gastrointestinal cytoprotective effects of the prostaglandins are known. See for example U.S. Pat. No. 4,083,998 (Robert, "Treatment of Inflammatory Disease of the Mammalian Large Intestine with Cytoprotective Prostaglandins"), issued April 11, 1978, U.S. Pat. No. 4,081,553 (Robert, "Cytoprotective Prostaglandins for Use in Intestinal Diseases"), issued Mar. 28, 1978, and U.S. Pat. No. 4,097,603 (Robert, "Gastric Cytoprotection with Non-antisecretory Doses of Prostaglandins"), issued June 27, 1978. Robert, in Gastroenterology 78:1245 (1980), discloses that certain prostaglandins are effective in preventing colitis produced by the proliferation of toxin-producing clostridium in antibiotic-treated hamsters. A number of prostaglandins and prostaglandin-like compounds are known to be bacteriacidal or antimicrobial, see, e.g., Derwent Farmdoc Nos. 33613C; 90067C; 87601B; 77055B; 31465B; 19942B; 15606B; 86540Y; 77386Y; 62899Y; 45139Y; 75530X; 73899X; 68620X; 25001X; 42571W; 24030W; 39858V; and 03817T.

SUMMARY OF THE INVENTION

The present invention particularly provides a method of preventing the release of toxins from bacteria which comprises contacting the bacteria with an amount of an antitoxic prostaglandin effective to prevent bacterial toxin release.

The present invention also provides a method for treating a toxin associated bacterial disease except those associated with the mammalian large intestine in an animal suffering from or susceptable to said diseases which comprises administering to said animal an amount of an antitoxic prostaglandin effective to prevent bacterial toxin release.

This invention further provides:

(1) in a method for treating a toxin-associated bacterial disease with one or more known antibiotics, the improvement which comprises: concomitantly administering an amount of an antitoxic prostaglandin which, together with said known antibiotics is effective to treat said toxin associated bacterial disease; and (2) in a unit dose of a pharmaceutical composition for treating a toxin-associated bacterial disease with one or more known antibiotics, the improvement which comprises: an amount of an antitoxic prostaglandin which, together with said known antibiotics, is an effective unit dose to treat said toxin-associated bacterial disease.

By the term "antitoxic prostaglandin" is meant all prostaglandins which decrease the amount of toxin released from C. difficile by at least 90% in the assay described in Example 1 when a pharmacologically practical amount of the prostaglandin is employed. These antitoxic prostaglandins are not antimicrobial or bacteriacidal compounds. Such prostaglandins include 16,16-dimethyl-PGE$_2$, 15(S)-15-methyl-PGE$_2$, 15(S)-16,16-trimethyl-PGE$_2$, as well as the methyl, (p-acetamidobenzamido)phenyl, and 1-(p-benzaldehyde-semicarbazone) esters thereof. The term "antitoxic prostaglandin" is also meant to include prodrugs of these compounds.

The bacteria treated by the method of the present invention are any bacteria which produce toxins associated with or contributing to the pathogenesis of a disease. Representative toxin-induced or associated diseases include those listed in Table I.

The present invention includes the treatment of each of the various mammalian species, including humans. With respect to non-humans, the present invention is particularly and especially concerned with treating domesticated animals, for example, cattle, dogs, cats, and swine. By treatment is meant any alleviation of symptoms caused by bacterial toxins. By prevention of toxin release is meant partial to total avoidance of the release of a toxin, and this term also includes the inhibition of the synthesis of a toxin by the bacteria, if such occurs.

By a "pharmacologically practical amount of prostaglandin" is meant an amount of prostaglandin, which, when administered to an animal, is efficacious in producing the desired result with minimal side effects and toxicity. Pharmacologically practical amounts of prostaglandins are typically in the range of 0.01 micrograms to 100 mg/kg.

By "prodrug" is meant a compound which, while not active by itself, is converted in the animal's system to an active compound. Thus, for example, 15(R)-15-methyl-PGE$_2$ by itself is not highly effective as an antitoxic prostaglandin. However, in mammalian metabolism it is converted by acid in the stomach to 15(S)-15-methyl-PGE$_2$, which is effective as an antitoxic prostaglandin. Thus, the term prodrug is meant to include all compounds which are converted to active compounds in the host's system. Such compounds are frequently employed for various pharmacological purposes due to their specific properties, e.g., delayed response and longer half life.

The method of the present invention can be used to block the release of toxins in a variety of situations. The preferred method of using the present invention is to prevent the release of cytotoxins from bacteria in animals and particularly humans. For humans an effective amount of an antitoxic prostaglandin is from 0.01 to 200 micrograms per 70 kg person up to 4 times daily. For other animals, an effective amount is from 0.01 micrograms to 1 mg/kg per day. The effective amount of an antitoxic prostaglandin as noted above is based on prostaglandins having a potency approximately equivalent to 16,16-dimethyl-$PGE_2$ in the assay described in Example 1. Greater or lesser amounts of other prostaglandins may be used, depending on their potency as compared to 16,16-dimethyl-$PGE_2$. An ordinarily skilled phamacologist will readily determine an equivalent amount of a particular prostaglandin, once potency versus 16,16-dimethyl $PGE_2$ is established.

Any convenient route of administration is employed. Thus, oral formulation and oral administration is, for example, the preferred route for use in humans although parenteral (e.g., intravenous, intraperitoneal, and intramuscular) administration and topical administration are also employed. See, e.g., U.S. Pat. No. 3,903,297 (Robert, "Method of Treatment in Prophylaxis of Gastric Hypersecretion in Gastric Acid and Duodenum Ulcers Using Prostaglandin Analogs"), issued Sept. 2, 1975, columns 6-16 and U.S. Pat. No. 4,009,282 (Vorhees, "Treatment of Proliferating Skin Diseases with Prostaglandins"), for some appropriate and well known means of administering the prostaglandins discussed herein.

The compounds of the present invention may also be administered topically, in the form of ointments, gels, and the like by means well-known in the art. Topical administration is employed, for example, in cases where the toxin-associated bacterial disease is localized in a particular area of the skin of the mammal. For a further discussion of the topical administration of prostaglandins see U.S. Pat. No. 4,009,282.

The dosage regimen for the antitoxic prostaglandin in accord with this invention will depend on a variety of factors including the type, age, weight, sex, and medical condition of the mammal, nature and severity of the bacterial disease and the particular prostaglandin to be administered. It is within the skill of the attending physician or veterinarian to determine the presence of the toxin associated bacterial disease, and to prescribe an effective amount of the prostaglandin to reduce and then substantially to eliminate the symptoms caused by the toxin.

The use of the antitoxic prostaglandins is, by a further embodiment of the present invention, undertaken concomitantly with other forms of conventional therapy for toxin-associated bacterial diseases. Such other forms of conventional therapy include, for example, the various chemical therapies described for example in The Merck Manual, pp. 103-112 (13th Ed. 1977); and Goth, Medical Pharmacology, pp. 581-615 (9th Ed. 1978). When such combination therapies are employed, significant effects are often obtained with reduced effective dosages of the compounds employed herein.

In accordance with this further embodiment of the present invention, there are provided novel pharmaceutical compositions for antibacterial therapy. These novel compositions consist of combinations of two or more active agents, one such agent being an antitoxic prostaglandin and the second and further agents being the heretofore known agents for the treatment of toxin-associated bacteria. Such previously known antibiotic agents include for example, ampicillin, carbenicillin, cepholothin, cephaloridine, cephalexin, cefazolin, methicillin, oxacillin, dicloxacillin, nafcillin, hetacillin, penicillin G, benzathine, penicillin G, various sulfonamides, vacomycin hydrochloride, novobiocin, lincomycin, and clindamycin. Such novel compositions are advantageously used in treating toxin-bacterial diseases, often permitting a reduced dosage of the instant antitoxic prostaglandin than that which would be required were it the sole therapy for treating toxin associated bacterial disease.

In these novel pharmaceutical compositions, the instant prostaglandins are employed for each unit dosage in an amount equal to the amount of the compound were it the sole therapy down to not less than 10% thereof. The other conventional antibiotic agent or agents are present therein at the known amounts employed in the treatment of toxin associated bacterial diseases. An ordinarily skilled physician or veterinarian can readily determine an effective amount of the conventional antibiotic agent to be employed.

Animals susceptible to bacterial toxin diseases include any animal recently exposed to a toxin producing bacteria. The conditions for exposure to toxin producing bacteria are well known. See, e.g., The Merck Manual, supra.

The method of the present invention may also be used to prepare antibodies or antitoxins in certain laboratory animals to be administered to humans or domesticated animals. Thus, a toxin-producing bacteria can be administered to a rabbit which is known to produce antibodies to the bacteria when administered in small amounts. An antitoxic prostaglandin can be administered to the rabbit so that the animal is protected from the ill effects of the toxin while it is forming antibodies to the bacteria. The antibody is then extracted from the rabbit and administered to the human or other animal suffering from, or susceptible to, a toxin associated bacterial disease.

The method of the present invention may further be employed to inhibit toxin release in vitro. Typically, an effective amount of an antitoxic prostaglandin for in vitro use is an amount such that the final concentration is from 0.1 micrograms to 10 mg/ml.

Thus, this method can be used to formulate vaccines for the use and prevention of a variety of bacterial diseases for which it was not previously advantageous to prepare a vaccine. A culture of the bacterial cells could be grown in the presence of an antitoxic prostaglandin. These cells could then be killed, formulated into a vaccine, and administered to a patient to immunize the patient against the bacterial disease. Previously, this would not always be practical to do in the case of toxin producing bacteria because of the possibility that toxin would be produced in vitro and thus introduced to the patient. By contacting the bacteria with an antitoxic prostaglandin, the danger of introducing the toxins to the patient is reduced.

The method of the present invention may also be employed in fermentation processes wherein bacteria are used to synthesize commercially important products. An aspect of new "genetic engineering" technology has been the ability to create bacteria which produce certain useful compounds. However, if toxin-producing bacteria are used, they may contaminate the final product. An antitoxic prostaglandin is thus added to the mixture to prevent the release of the toxin. Prostaglandins are generally easier to extract from the final product than toxins and further, relatively smaller amounts of prostaglandin are used.

Thus, the method of the present invention is employed any time it is desirable to inhibit bacterial toxin release, whether in vitro or in vivo. Thus, the method is useful for various medical, pharmacological, and synthetic purposes.

DESCRIPTION OF THE PREFERRED EMBODIMENTS

The operation of the present invention is seen more fully by the examples given below.

EXAMPLE 1

Forty-five filtrates of *C. difficile* cultures grown in the presence of different concentrations of 16,16-dimethyl-$PGE_2$ were assayed for cytotoxin. (ATCC 9689 stands for American Type Culture Collection number 9689, and patients 1, 2, 3, and 4 refer to cultures extracted from various hospital patients.) The first 25 cultures were incubated with the prostaglandin (in the concentrations noted) for 24 hr. These cultures were then filtered and the supernate was submitted for cytotoxicity testing. The remaining 20 cultures were incubated without prostaglandin, filtered and then the prostaglandin was added to each supernate prior to cytotoxicity testing. The cytotoxin assay utilized human skin fibroblasts (HFF) as mono-layers in Costar 24 well-trays. The results are presented as the reciprocal of the cytotoxin dilution (serial 10-fold) causing altered cell morphology for 50% of the cells in the mono-layer. (see Table II.) Thus, 1000 means that a 1:1000 dilution of the filtrate caused an altered cell morphology for 50% of the cells in the mono-layer. Therefore, the higher the number, the more cytotoxin is present. As can be seen, as the amount of prostaglandin increases, the amount of toxin decreases.

EXAMPLE 2

To determine whether the presence of 16,16-dimethyl-$PGE_2$ might interfere with the cytotoxin assay, several concentrations of cytotoxins were assayed in the presence of various concentrations of a prostaglandin.

The cytotoxins used were from hamster cecum, a filtrate of *C. difficile* broth culture, and the filtate of human feces from a patient with "antibiotic diarrhea". Serial 10-fold dilutions of the cytotoxins were prepared in BME-3% fbs. (BME 3% fbs is basal medium of Eagle with 3% fetal bovine (BOVINE Serum and antibiotics.))

16,16-Dimethyl-$PGE_2$ (5 mg/ml in absolute ethanol) was used and further diluted in absolute ethanol.

Human skin fibroblasts (HFF) monolayers in wells of Costar trays (24 well) were refed with 0.8 ml BME-3% fbs. 0.1 ml of the various prostaglandin concentrations and absolute ethanol alone were added to the appropriate wells. Separate wells were then treated with (0.1 ml) of the appropriate dilution of each cytotoxin. The trays were incubated at 37° and examined microscopically for evidence of altered cell morphology.

The results (Table III) using cytotoxins from three different sources show that 16,16-dimethyl-$PGE_2$ was ineffective in protecting fibroblasts from morphological changes due to the action of the cytotoxin. These data show that the prostaglandin did not affect the interaction of the cytotoxin with the cell.

TABLE I

| Toxin Producing Bacteria | |
|---|---|
| Bacterial Species | Diseases |
| *Clostridium botulinum* | Botulism |
| *Clostridium tetani* | Tetanus |
| *Clostridium perfringens* | Gas gangrene |
| *Clostridium sepicum* | Gas gangrene |
| *Clostridium novyi* | Gas gangrene |
| *Corynebacterium diphtheriae* | Diphtheria |
| *Staphylococcus aureus* | Pyogenic infections and Mastitis |
| *Streptococcus pyogenes* | Pyogenic infections and Scarlet fever |
| *Pasteurella pestis* | Plague |
| *Bordetella pertussis* | Whooping cough |
| *Shigella dysenteriae* | Dysentery |
| *Vibrio cholera* | Cholera |
| *Propionibacterium* | Acne |

TABLE II

| Code # | Cytotoxin Dilution | *C. difficile* strain | Prostaglandin mcg/ml |
|---|---|---|---|
| Prostaglandin Incubated with *C. difficile* | | | |
| 1 | 1000 | ATCC #9689 | 0 |
| 2 | 100–1000 | ATCC #9689 | 1 |
| 3 | 100 | ATCC #9689 | 10 |
| 4 | 10 | ATCC #9689 | 50 |
| 5 | 1000 | Patient 1 | 0 |
| 6 | 100–1000 | Patient 1 | 1 |
| 7 | 10 | Patient 1 | 10 |
| 8 | 10 | Patient 1 | 50 |
| 9 | <10 | Control | 0 |
| 10 | <10 | Control | 1 |
| 11 | <10 | Control | 10 |
| 12 | <10 | Control | 50 |
| 13 | 100 | Patient 2 | 0 |
| 14 | 10–100 | Patient 2 | 1 |
| 15 | 10–100 | Patient 2 | 10 |
| 16 | <10 | Patient 2 | 50 |
| 17 | <10 | Patient 3 | 0 |
| 18 | <10 | Patient 3 | 1 |
| 19 | <10 | Patient 3 | 10 |
| 20 | <10 | Patient 3 | 50 |
| 21 | 100–1000 | Patient 4 | 0 |
| 22 | 100 | Patient 4 | 1 |
| 23 | 10–100 | Patient 4 | 10 |
| 24 | 10 | Patient 4 | 50 |
| 25 | <10 | 1% alcohol vehicle | 0 |
| Prostaglandin Added After Incubation | | | |
| 26 | 100–1000 | ATCC #9689 | 0 |
| 27 | 100–1000 | ATCC #9689 | 1 |
| 28 | 10–100 | ATCC #9689 | 10 |
| 29 | 10 | ATCC #9689 | 50 |
| 30 | 100–1000 | Patient 1 | 0 |
| 31 | 1000 | Patient 1 | 1 |
| 32 | <100 | Patient 1 | 10 |
| 33 | 100 | Patient 1 | 50 |
| 34 | 10–100 | Patient 2 | 0 |
| 35 | 10 | Patient 2 | 1 |
| 36 | 10 | Patient 2 | 10 |
| 37 | <10 | Patient 2 | 50 |
| 38 | <10 | Patient 3 | 0 |
| 39 | <10 | Patient 3 | 1 |
| 40 | <10 | Patient 3 | 10 |
| 41 | <10 | Patient 3 | 10 |
| 42 | 100 | Patient 4 | 0 |
| 43 | 100–1000 | Patient 4 | 1 |
| 44 | 100 | Patient 4 | 10 |
| 45 | 10–100 | Patient 4 | 50 |

TABLE III

Attempted protection of HFF from cytotoxins from different sources by 16,16-dimethyl-PGE$_2$. The results are expressed as the number of cells showing evidence of altered morphology due to cytotoxin. (0 = no change, +1 = 25% of the cells are rounded, +2 = 50% of the cells are rounded, +3 = 75% of the cells are rounded, and +4 = 100% of the cells are rounded. Tox = toxic concentration of prostaglandin.)

| Cyto-toxin: | Cyto-toxin Dilution | Prostaglandin Concentrations (mcg/ml) | | | | | |
|---|---|---|---|---|---|---|---|
| | | 100 | 10 | 1 | 0.1 | 0.01 | Cont |
| Hamster | 1:10 | tox | +4 | +4 | +4 | +4 | +4 |
| | 1:100 | tox | +4 | +4 | +4 | +4 | +4 |
| | 1:1000 | tox | +4 | +4 | +4 | +4 | +4 |
| | control | tox | 0 | 0 | 0 | 0 | 0 |
| *C. diffi-cile* filtrate | 1:10 | tox | 4 | 4 | 4 | 4 | 4 |
| | 1:100 | tox | 4 | 4 | 4 | 4 | 4 |
| | 1:1000 | tox | 3 | 3 | 3 | 3 | 3 |
| | control | tox | 0 | 0 | 0 | 0 | 0 |
| Human | 1:10 | tox | 4 | 4 | 4 | 4 | 4 |
| | 1:100 | tox | 3 | 4 | 4 | 4 | 4 |
| | 1:1000 | tox | 1 | 1 | 1 | 1 | 1 |
| | control | tox | 0 | 0 | 0 | 0 | 0 |

We claim:

1. A method of preventing the release of toxins from bacteria capable of releasing a toxin which comprises contacting the bacteria with an amount of an antitoxic, non-antibicrobial, and non-bacteriacidal prostaglandin effective to prevent toxin release.

2. A method of claims 1 or 2 wherein said prostaglandin is 16,16-dimethyl-PGE$_2$.

3. A method for treating toxin associated bacterial diseases except those associated with the mammalian large intestine in an animal suffering from or susceptable to said diseases which comprises administering to said animal an amount of an antitoxic, non-antibicrobial, and non-bacteriacidal prostaglandin effective to prevent toxin release.

4. A method of claim 3 wherein said animal is a human.

5. A method of claim 4 wherein said prostaglandin is 16,16-dimethyl-PGE$_2$.

6. In a method for treating a toxin-associated bacterial disease with one or more known antibiotics, the improvement which comprises:
concomitantly administering an amount of an antitoxic non-antimicrobial, and non-bacteriacidal, prostaglandin which, together with said known antibiotics is effective to treat said toxin associated bacterial disease.

7. A method of claim 6 wherein said prostaglandin is 16,16-dimethyl PGE$_2$.

8. In a unit dose of a pharmaceutical composition for treating a toxin-associated bacterial disease with one or more known antibiotics, the improvement which comprises:
an amount of an antitoxic, non-antimicrobial, and non-bacteriacidal prostaglandin which, together with said known antibiotics, is an effective unit dose to treat said toxin-associated bacterial disease.

9. A unit dose of claim 8 wherein said prostaglandin is 16,16-dimethyl PGE$_2$.

* * * * *